United States Patent [19]

Dorman et al.

[11] Patent Number: 5,154,749
[45] Date of Patent: Oct. 13, 1992

[54] HERBICIDAL LATEX DISPERSION FOR CONTROLLED DELIVERY AND RELEASE OF HERBICIDES AND THEIR PREPARATION

[75] Inventors: Linneus C. Dorman, Midland, Mich.; Paul A. Meyers, Dublin, Calif.

[73] Assignee: DowElanco, Indianapolis, Ind.

[21] Appl. No.: 314,526

[22] Filed: Feb. 23, 1989

Related U.S. Application Data

[63] Continuation-in-part of Ser. No. 127,573, Dec. 3, 1987, abandoned, which is a continuation of Ser. No. 795,031, Nov. 4, 1985, abandoned.

[51] Int. Cl.⁵ ............................................. A01N 43/20
[52] U.S. Cl. ......................................... 71/88; 71/126; 71/DIG. 1
[58] Field of Search ...................... 71/88, 126, DIG. 1

[56] References Cited

U.S. PATENT DOCUMENTS

| | | | |
|---|---|---|---|
| 3,156,661 | 11/1964 | Feinberg | 514/475 |
| 3,212,967 | 10/1965 | McFadden et al. | 71/DIG. 1 |
| 3,400,093 | 9/1968 | Feinberg | 424/78 |
| 4,129,435 | 12/1978 | Takematsu | 71/65 |
| 4,211,549 | 7/1980 | Markley et al. | 71/88 |
| 4,303,642 | 12/1981 | Kangas | 424/78 |
| 4,304,769 | 12/1981 | Chen | 424/218 |
| 4,336,173 | 6/1982 | Ugelstad | 523/205 |
| 4,337,185 | 6/1982 | Wessling et al. | 524/458 |
| 4,512,969 | 4/1985 | Chen | 424/81 |

OTHER PUBLICATIONS

Danielson et al., Proc. of the Controlled Release Pesticide ym., p. 41-A.1, 1975.
Bioactive Materials, pp. 12-16, 1980.
Bode et al. Circular 1192, Equipment and Calibration; Low Pressure Sprayers, May 1981.
Banker, Abs. of the 7th Int'l Sym on Controlled Release of Bioactive Materials, pp. 12-16, 1980.
Boylan and Banker, J. Pharm. Sci, 62, 1177 (1973).
Freidhoff, Diss., Abst. Int. B, 37, 540 (1976).
Vanderhoff et al., Makromol. Chem., Suppl. 10/11 391-402 (1985).
Agricultural Products Test Methods Manual CH-137:-Pre-Emergence Herbicide.
Doane's Facts & Figures for Farmers, Doane-Western, Chap. 25, pp. 244-287 Copyright 1981.

*Primary Examiner*—Richard L. Raymond
*Assistant Examiner*—B. M. Burn
*Attorney, Agent, or Firm*—S. Preston Jones; Kenneth L. Loertscher

[57] ABSTRACT

A controlled release and delivery system for a hydrophobic, water sensitive herbicide is produced by:
(a) dissolving the herbicide in a volatile water-immiscible solvent;
(b) introducing the solvent containing the herbicide dissolved therein to a latex dispersion comprising an aqueous continuous phase and polymeric discrete phase;
(c) agitating the resultant mixture until the polymeric particles of the discrete phase absorb the herbicide; and
(d) removing the solvent from the resultant mixture at reduced pressure.

20 Claims, No Drawings

HERBICIDAL LATEX DISPERSION FOR CONTROLLED DELIVERY AND RELEASE OF HERBICIDES AND THEIR PREPARATION

RELATIONSHIP TO PRIOR APPLICATIONS

This is a continuation-in-part of Application Ser. No. 127,573, filed Dec. 3, 1987, now abandoned, which in turn is a continuation of Application Ser. No. 795,031, filed Nov. 4, 1985, now abandoned.

BACKGROUND OF THE INVENTION

Controlled release and delivery systems for herbicides are known and can be achieved by:

(a) combining acidic herbicides, e.g., 2,4-dichlorophenoxyacetic acid, with basic polymers, e.g., a polyvinyl-amine, to form herbicide-polymer salts;

(b) utilization of rubbers and elastomers as matrix reservoirs;

(c) use of a herbicide-containing polymer emulsion;

(d) utilization of biodegradable polymers as matrices, e.g., polyureas, polyacetals, cellulose derivatives, polyesters and polyurethanes;

(e) use of synthetic and natural polymeric materials containing covalently-bound pendant herbicide groups;

(f) utilization of inorganic materials such as glass, clays and plaster of Paris as well as organic polymers to incorporate herbicides in pellets and granules; and (g) encapsulation of herbicides in polymers. U.S. Pat. No. 4,304,769 to Chen discloses "loaded" polymeric latex compositions and their preparation. U.S. Pat. No. 4,303,642 to Kangas discloses stable latexes comprising polymers which contain insecticides.

U.S. Pat. No. 3,156,661 to Feinberg discloses the use of styrene latexes as carriers of insecticidal materials. U.S. Pat. No. 4,336,173 to Ugelsad discloses a process for preparing an aqueous emulsion of a partly water-soluble material. Banker and Boylan have reported the use of latexes and pseudolatexes to entrap drugs and insecticides for controlled release. Banker, *Abs. of the 7th Int'l. Sym. on Controlled Release of Bioactive Materials*, pp. 12–16, 1980, and Boylan and Banker, *J. Pharm. Sci.*, 62, 1177 (1973).

There are several advantages of using a latex for a herbicide controlled delivery system over conventional polymer matrices. First, latexes by their own unique nature exist in stable colloidal form and as such can be easily diluted with water and applied to the soil with conventional spray or aqueous dispersal systems; conventional herbicide containing polymer matrices would have to be converted to some dispersible form, i.e., pellets, granules or an emulsion before they could be applied; none of these physical processes, however, can readily produce small particles equal in size to typical latexes, i.e., about 0.1–1.5 μm, hence the dispersibility of the herbicide in the latex particles is much greater and the resulting greater surface area of the latex particles might afford a better release profile. A second advantage is that commercial latexes can be produced in essentially monodisperse form without the need of further sorting, thereby assuming uniform distribution during application. A third advantage of latex is that many polymers like polyesters, polyamides and polyurethanes are more expensive than some commercial latex polymers and their processes and starting monomers may be more expensive than latex polymers.

A latex controlled delivery system also offers an additional advantage over polymer matrices containing chemically attached pendant herbicide molecules. For example, chemically-attached herbicides, e.g., via ester functions, must undergo hydrolysis to be effective, and the rate of hydrolysis is very much dictated by the extent of moisture in the immediate environment; therefore, the use of chemically-bound herbicide polymers must be confined to environments where the water content is always predictable. In latex systems, after dispersal of the colloidal herbicide containing polymer particles, the presence or absence of environmental water is not critical for release of the herbicide.

The processes of the prior art are disadvantageous, however, when dealing with hydrophobic, hydrolyzable herbicides. Use of a water-miscible solvent as disclosed in U.S. Pat. No. 4,304,769 with a hydrophobic material such as the herbicides contemplated by this invention results in the destabilization of the latex dispersion. When a hydrophobic herbicide material is dissolved in a water-miscible solvent and this solution is brought together with the latex dispersion, the water-miscible solvent blends with the water int eh latex dispersion but this blend of water and the water-miscible solvent is incapable of maintaining the water-insoluble herbicide material in solution. Consequently, the insoluble herbicide material separates form the water/water miscible solvent blend, as an oil, or as a colloid, i.e., in finely dispersed form. For example, when an acetone solution of tridiphane is mixed with water, the tridiphane separates form the resulting water-acetone solution.

Where the herbicide used is subject to substantial hydrolysis over time, it tends to undergo decomposition upon exposure to water, and the use of heat to form the latex dispersion, as taught in U.S. Pat. No. 4,303,642, causes the hydrophobic herbicide to undergo hydrolysis more readily, especially in the absence of any solvent as taught by the reference process.

Objects of the Invention

It is an object of this invention to provide a controlled delivery and release system for hydrophobic, hydrolyzable herbicides selected from the group consisting of
1,1,1-trichloro-3,4-epoxy-3-(3,5-dichlorophenyl)butane;
1,1,1-trichloro-3,4-epoxy-3-(3,5-dibromophenyl)butane;
1,1,1-trichloro-3,4-epoxy-3-(3,5-dimethylphenyl)butane;
1,1,1-trichloro-3,4-epoxy-3-(3,5-chlorophenyl)butane;
2,2-dichloro-4,5-epoxy-4-(3,5-dichlorophenyl)pentane;
α-(2,2,2-trichloroethyl)-3,5-dichlorostyrene;
α-(2,2,2-dichloropropyl)-3,5-dichlorostyrene; and
α-(2,2,2-trichloroethyl)-3,5-dibromostyrene.

It is another object to provide a method for producing such a system.

Upon further study of the specification and appended claims, further objects and advantages of this invention will become apparent to those skilled in the art.

SUMMARY OF THE INVENTION

In a process aspect, this invention relates to a method for preparing a herbicidal latex dispersion comprising an aqueous continuous phase and a polymeric discrete phase wherein the polymeric particles of the discrete phase contain a hydrophobic herbicide susceptible to hydrolysis selected from the group consisting of 1,1,1-trichloro-3,4-epoxy-3-(3,5-dichlorophenyl)butane;
1,1,1-trichloro-3,4-epoxy-3-(3,5-dibromophenyl)butane;
1,1,1-trichloro-3,4-epoxy-3-(3,5-dimethylphenyl)butane;
1,1,1-trichloro-3,4-epoxy-3-(3-chlorophenyl)butane;
2,2-dichloro-4,5-epoxy-4-(3,5-dichlorophenyl)pentane;
α-(2,2,2-trichloroethyl)-3,5-dichlorostyrene;
α-(2,2,2-dichloropropyl)-3,5-dichlorostyrene; and
α-(2,2,2-trichloroethyl)-3,5-dibromostyrene;
which comprises:
  (a) dissolving the hydrophobic herbicide in a volatile water-immiscible solvent;
  (b) introducing the solvent containing said herbicide dissolved therein into a two phase latex dispersion comprising an aqueous continuous phase and a polymeric discrete phase having absorption capacity for said herbicide;
  (c) agitating the resultant mixture for a time sufficient for the polymeric particles of the discrete phase to absorb the herbicide therein; and
  (d) removing the solvent form the resultant mixture at reduced pressure.

In a product aspect, this invention also relates to the thus-produced novel herbicide-containing latex dispersions.

DETAILED DISCUSSION

The latex dispersion comprises an aqueous continuous phase and a polymeric discrete phase wherein the polymeric particles of the discrete phase contain the hydrophobic herbicide susceptible to hydrolysis.

Latexes employed in step (b) of the above-defined process of the invention have a high absorption capacity for the hydrophobic herbicide, preferably 20 percent to 95 percent wt/wt, and most preferably 90 percent to 95 percent wt/wt, calculated on the polymer solids. Operable latexes include conventional aqueous emulsions of polymers, e.g., those employed to produce coatings, such as polystyrene, polyvinyltoluene and polyvinylacetate.

Illustrative of the latexes usable in the practice of the present invention are those derived from
  (a) monovinylidene carbocyclic monomers, such as, styrene; styrene ring-substituted by methyl, two methyl groups, ethyl, tert-butyl, cyano, hydroxy, methoxy, ethoxy, or, a methyl and a chloro group; and vinylnaphthylene;
  (b) a combination of one of the foregoing monovinylidene carbocyclic monomers with an emulsion-polymerizable co-monomer in the nature of co-polymerizable latex stabilizer having from 3 to about 26 carbon atoms;
  (c) an ester of an α,β-ethylenically unsaturated carboxylic acid having about 3-9 carbon atoms, e.g., methyl methacrylate, chloroethyl methacrylate, n-butyl methacrylate, cyclohexyl chloroacrylate, ethyl chloroacrylate, methyl chloroacrylate, and isopropyl chloroacrylate; and
  (d) α,β-ethylenically unsaturated esters of non-polymerizable carboxylic acids, e.g., vinyl acetate, vinyl propionate, vinyl benzoates optionally carrying a ring substitutent such as lower alkyl of 1 to 4 carbon atoms, lower alkoxy of 1 to 4 carbon atoms, halo, cyano, or hydroxy, e.g., ethyl, vinyl toluate, allyl benzoates, vinyl pivalate and other such monomers wherein the unsaturated group has about 2-14 carbon atoms.

Of the foregoing monomers, the monovinylidene carbocyclic monomers, and particularly styrene and mixtures of styrene and itaconic acid, and α,β-ethylenically unsaturated esters of non-polymerizable carboxylic acids, particularly vinyl acetate, are especially preferred.

Preferred polymer solids content of the latexes are from about 20-25 percent. With most latexes, water can be added to reduce the polymer solids content thereof, e.g., to render the emulsion more readily sprayable and to provide latexes having a solids content in the preferred range. When polystyrene latex is used, solids content generally ranges from about 1–50 percent, with about 50 percent being preferred. Particle size can range from about 300–10,000 Å, preferably from about 500–1500 Å, e.g., about 1400 Å, when polystyrene latex is used.

Herbicides employed in the present invention are well known active herbicides and are hydrophobic and subject to hydrolysis. The term "hydrophobic" mans less than about 10 ppm of the herbicide by weight is soluble in water. The term "subject to hydrolysis" means that at least 15 percent of the herbicidal activity is lost per week at ambient summer temperatures. Examples of such herbicides include:

1,1,1-trichloro-3,4-epoxy-3-(3,5-dibromophenyl)butane;
1,1,1-trichloro-3,4-epoxy-3-(3,5-dimethylphenyl)butane;
2,2-dichloro-4,5-epoxy-4-(3,5-dichlorophenyl)pentane;
α-(2,2,2-trichloroethyl)-3,5-dichlorostyrene;
α-(2,2,2-dichloroethyl)-3,5-dichlorostyrene;
α-(2,2,2-trichloroethyl)-3,5-dibromostyrene;
1,1,1-trichloro-3,4-epoxy-3-(3,5-chlorophenyl)butane;

A preferred hydrophobic, hydrolyzable herbicide is tridiphane (1,1,1-trichloro-3,4-epoxy-3-(3,5-dichlorophenyl)butane).

Herbicide concentrations can range from about 20–95 percent by weight relative to the latex polymer solids content. Preferred concentrations are about 95 percent. Tridiphane is generally used at concentrations from about 75–95 percent by weight of polymer solids, with about 95 percent being preferred.

Solvents operable in the process of the invention are characteristically water-immiscible and relatively volatile. A water-immiscible, volatile solvent functions to protect the herbicide from hydrolysis by water during processing, to efficiently transfer the herbicide tot he polymer phase of the latex without destabilizing the latex (because only a minimal amount of the solvent is necessary), to enable removal of the solvent under mild processing conditions and recyclization of the solvent for further use, and to incorporate high concentrations of th herbicide into the polymer phase.

Preferred solvents have boiling points ranging from about 35° C.–125° C., preferably 35° C.–70° C. Suitable solvents include hydrocarbons of up to 7 carbon atoms, preferably benzene, cyclohexane, cyclopentane, heptane, hexane, methylcyclohexane, 2-methylhexane, 3-methylhexane, 2-methylpentane, 3-methylpentane, pentane or toluene; halogenated hydrocarbons of up to 2 carbon atoms, preferably carbon tetrachloride, chloroform, methylene chloride, ethylene dichloride, trichloroethane; and sulfur-containing solvents of up to 2 carbon atoms, preferably carbon disulfide or methyl sulfide.

The amount of a given solvent to be used will vary according to the solubility therein of the herbicide used and the extent of any swelling that the solvent induces in the polymer particles of ht latex, i.e., excessive swelling of the latex polymer particles is to be avoided to prevent their coalescence into a single polymer phase. Preferably, a solvent is selected in which the herbicide is vary soluble, thereby avoiding the use of excessive amounts of solvent. These are parameters understood by those skilled in the art, and proper quantities can be determined by one so skilled in accordance with conventional laboratory and production techniques and based on the examples presented herein. Preferred solvent concentrations are about 0.7-2 ml/g of herbicide. Concentrations of hexane where tridiphane is used are about 0.7-1 ml/g of tridiphane, with about 0.8 ml/g being preferred.

The aqueous phase optionally contains a surfactant conventionally employed in agricultural chemical/resin compositions. Preferably, a nonionic surfactant is employed. Preferred surfactants include Dowfax ® 9N10 and Triton ® X-100.

Surfactant content in the composition can range from about 1-20 percent. Triton ® X-100 is generally used at concentrations from about 2-15 percent by weight relative to latex polymer solids content, with 10 percent by weight being preferred.

In step (a) of the process, the herbicide is dissolved in the volatile water-immiscible solvent, e.g., at ambient temperature. In step (b), the resultant solution is mixed with the latex, preferably by slowly adding the former to the latter, also at ambient temperature. In step (c), the mixture is agitated at ambient temperature, generally for about 10-24 hours, preferably about 15-20 hours, to ensure that the maximum amount of herbicide is loaded, i.e., absorbed into the latex particles. In step (d) of the process, the solvent is removed under reduced pressure with heat being applied as deemed appropriate by those skilled in the art considering the relative volatility of the solvent employed. As an example, for hexane, the preferred conditions for solvent removal are 90 to 200 mm/Hg pressure and a temperature of 25°-40° C.

The latex dispersion functions as a controlled delivery system for the herbicide since the dispersion can be readily diluted with water and applied preemergently to the soil using conventional aqueous spraying equipment. The herbicides-latex dispersion is also a controlled release system since loss of the herbicide from the soil by evaporation and/or degradation is reduced owing to its mediated release from the polymer phase of the latex dispersion. A tridiphane-latex dispersion can be used efficaciously for the control of grasses in corn.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples all temperatures are set forth uncorrected in degrees Celsius and unless otherwise indicated, all parts and percentages are by weight. The term "Herbicide content" refers to the amount of the herbicide actually loaded into the polymer.

EXAMPLE 1

A mixture of 20.6 g (10.1 g polymer solids) of 1400 Å diameter polystyrene latex (Dow plastic pigment No. 788) that has been itaconic acid stabilized and contains 48.6 percent polymer solids, 1 g of Triton ® X-100 and 25 ml of deionized water was shaken in a bottle to disperse the surfactant and the resulting mixture was transferred to a 3-necked, 250 ml round-bottomed flask equipped with an air stirrer and propeller, a dropping funnel and condenser in the necks. To this briskly stirred mixture was added dropwise a solution of 10 go of tridiphane in 8 ml of hexane for 45 minutes. Stirring of the mixture was continued overnight. The mixture was then freed of hexane in vacuo (ca 210 mm at 40° C.). The preparation was then allowed to settle in a separatory flask. A small, brown layer composed of undissolved tridiphane and/or traces of flocculated latex particles settled out. The top layer was separated with the aid of a syringe. Water was added to the lower layer and the mixture was centrifuged to effect a faster separation of layers. The latex portions were combined and diluted to 90 g.

Upon analysis, the product was found to have a chlorine content of 5.92±0.1 percent, corresponding to a tridiphane content of 10.7±0.2 percent (w/w) and an uptake of 96.3±1.8 percent, or 9.63 g of tridiphane. Polymer solids content was about 11.1 percent. Larger lots of this product were prepared for field trials by scaleup of this preparation.

In subsequent preparations the top product layer could be separated largely by careful decantation and the residual layer was rinsed with additional water and additional product was separated by decantation and combined with the initial product layer.

EXAMPLE 2

Tridiphane-Varied Size Polystyrene Latex Dispersions

Dispersions of tridiphane and polystyrene latexes (Aerosol ® MA stabilized) of sizes 1850, 3970 and 6515 Å were prepared by the general procedure describe in Example 1. The final latex had the properties listed below.

| | | | PRODUCT SUMMARY | |
|---|---|---|---|---|
| | | | Tridiphane | |
| Example | Latex (Å) | Polymer Solids (%) | % in Dispersion[a] | % of Uptake[b] |
| 2A. | 1850 | 12.1 | 11.5 | 94.9 |
| 2B. | 3970 | 10.7 | 10.4 | 97.0 |
| 2C. | 6515 | 10.7 | 10.6 | 98.2 |

[a]Based on chlorine analysis
[b]Efficiency of uptake

EXAMPLE 3

Dispersion Preparation Without Added Water

A charge of 24.6 g (10.1 g polymer solids) of the 1850 Å latex (40.7 percent solids) and 1 g of Triton ® X100 was stirred vigorously until the surfactant was evenly dispersed. A solution of 9.0 g of tridiphane in 7 ml (4.35 g) of hexane was added dropwise with vigorous stirring. Stirring was continued for 15 hours. The reaction mixture (38.9 g) was halved and one portion was freed of hexane in vacuo while the other was bottled without further treatment.

Hexane-free: about 29 percent polymer solids, tridiphane, 26.0 percent calculated, 27.2 percent found (by chlorine analysis).

Hexane-containing: about 26 percent polymer, solids, tridiphane, 23.1 percent calculated, 25.7 percent found (by chlorine analysis).

Similar dispersions with the 6515 Å latex (32.5 percent polymer solids) were also prepared.

These experiments demonstrate the feasibility of preparing latex dispersions of the herbicide, without added water, yielding preparations containing about 50 percent water.

EXAMPLE 4

A mixture of 81.7 g (39.7 g polymer solids) of polystyrene latex (Dow plastic pigment (DPP)-788; itaconic acid stabilized; 48.6 percent solids; 1400 Å particle diameter), 4 g of Triton ® X100 and 100 ml of deionized water was shaken in a closed bottle to disperse the surfactant and the resulting mixture was transferred to a liter, 3-necked Morton flask equipped with an air stirrer and propeller and a dropping funnel. To this briskly stirred mixture was added a solution of 38.1 g (96 percent of the weight of the latex polymer solids) of tridiphane (technical grade) in 33 ml of hexane during about 45 minutes. Stirring of the mixture was continued for 20 hours at ambient temperature. The mixture was then freed of hexane in vacuo at 34° C. (92 mm) for 2 hours. The residue was then diluted to 397 g yielding a product dispersion having complete uptake of biocide in the polymer phase (10 percent polymer solids and 9.6 percent tridiphane).

EXAMPLE 5

This example was carried out in the manner described in Example 1, using 20.2 g (10.1 g polymer solids) of about 1500 Å diameter polyvinyl acetate latex (Vinac, Air Products, 50.1 percent polymer solids), 1 g of Triton ® X100, 25 m of deionized water, 10 g of tridiphane and 8 ml of hexane. No undissolved tridiphane separated during the settling phase of the preparation. The smooth, white, homogeneous preparation was transferred from a small amount (<0.2 ml) of flocculated latex particles and diluted to 90 g with deionized water.

COMPARATIVE EXAMPLE A

Without Solvent Vehicle

The initial part of this preparation and charge was similar to that of Example 1. The stirred latex mixture was heated to 42° C., whereupon the tridiphane was added in small portions, time being allowed for each portion to melt before ht next was added, 15 minutes was required to complete the addition. Stirring at 42°-45° C. was continued for 0.5 hour. Heating was discontinued and stirring was continued for an additional 15 hours. The mixture was transferred to a separatory flask (some residual tridiphane had crystallized in the flask) and allowed to settle. Work-up of the preparation was achieved as hereinbefore; the preparation was finally diluted to 77 g.

A chlorine content of 6.29±0.1 percent, was found upon analysis of the product corresponding to a tridiphane content of 11.37±0.2 percent and an uptake of 87.5±1.6 percent, or 8.75 g of tridiphane.

Comparing the respective uptake results of Example 1 and Comparative Example A:

96.3±1.8 percent=94.5—98.1 percent vs.

87.5±1.6 percent=85.9—89.1 percent

These differences are significant, particularly when compared on an industrial scale, i.e., in magnitude of millions of pounds. Because the claimed process clearly achieves a more efficient uptake of the herbicide, herbicide loss due to hydrolysis is reduced, thereby reducing the amount of excess herbicide which must be present to ensure that label strength is met in the product as purchased.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing form the spirit and scope thereof, can make various changes and modifications of the invention to adapt it to various usages and conditions.

In tests designed to compare the herbicidal activity of the latex formulations of the active compounds of the present invention with conventional formulations of the same active compounds, it was found that the different formulations have substantially the same degree of herbicidal activity. This shows that the instant formulations do not degrade the herbicidal activity of the active compounds and that the latex formulations of the present invention can be employed in the same uses as conventional formulations with the added benefits of ht instant formulations.

What is claimed is:

1. A method for preparing a herbicidal latex dispersion comprising an aqueous continuous phase and a polymeric discrete phase wherein the polymeric particles of the discrete phase contain a hydrophobic herbicide susceptible to hydrolysis selected from the group consisting of tridiphane (1,1,1-trichloro-3,4-epoxy-3-(3,5-dichlorophenyl)butane;
1,1,1-trichloro-3,4-epoxy-3-(3,5-dibromophenyl)butane;
1,1,1-trichloro-3,4-epoxy-3-(3,5-dimethylphenyl)butane;
1,1,1-trichloro-3,4-epoxy-3-(3,5-chlorophenyl)butane;
1,1,1-trichloro-3,4-epoxy-3-(3,5-dichlorophenyl)pentane;
α-(2,2,2-trichloroethyl)-3,5-dichlorostyrene;
α-(2,2,2-dichloropropyl)-3,5-dichlorostyrene; and
α-(2,2,2-trichloroethyl)-3,5-dibromostyrene;

which comprises:
(a) dissolving the herbicide in a volatile water-immiscible solvent;
(b) introducing the solvent containing the herbicide dissolved therein to a latex dispersion comprising an aqueous continuous phase and polymeric discrete phase having herbicidal absorption capacity;
(c) agitating the resultant mixture for a time sufficient for the polymeric particles of the discrete phase to absorb the herbicide; and
(d) removing the solvent from the resultant mixture at reduced pressure.

2. The method of claim 1, wherein the herbicide is tridiphane.

3. The method of claim 1, wherein the solvent concentration in step (a) is about 0.7-2 ml per gram of herbicide.

4. The method of claim 3, wherein the solvent has a boiling point of about 35° C.–125° C.

5. The method of claim 4, wherein the solvent is a hydrocarbon of up to 7 carbon atoms, a halogenated hydrocarbon of up to 2 carbon atoms, or a sulfur-containing hydrocarbon of up to 2 carbon atoms.

6. The method of claim 5, wherein the solvent comprises hexane.

7. The method of claim 1, wherein the latex dispersion employed in step (b) has a polymer solids content of 20–50 percent by weight.

8. The method of claim 7, wherein the latex employed in step (b) is derived from (i) a monovinylidene carbocyclic monomer; (ii) a combination of a monovinylidene carbocyclic monomer and an emulsion-polymerizable co-monomer in the mature of a copolymerizable latex stabilizer having from 3 to about 26 carbon atoms; (iii) an ester of an $\alpha,\beta$-ethylenically unsaturated carboxylic acid having about 3 to 9 carbon atoms; or (iv) an $\alpha,\beta$-ethylenically unsaturated ester of non-polymerizable carboxylic acid.

9. The method of claim 8, wherein the latex employed in step (b) is derived from a monovinylidene carbocyclic monomer.

10. The method of claim 9, wherein the monovinylidene carbocyclic monomer is styrene.

11. The method of claim 8, wherein the latex employed in step (b) is derived from the combination of a monovinylidene carbocyclic monomer and an emulsion-polymerizable co-monomer.

12. The method of claim 11, wherein the latex employed in step (b) is derived from a combination of styrene and itaconic acid.

13. The method of claim 8, wherein the latex employed in step (b) is derived from an $\alpha$-$\beta$-ethylenically unsaturated ester of non-polymerizable carboxylic acid.

14. The method of claim 13, wherein the latex employed in step (b) is derived from vinyl acetate.

15. The method of claim 8, wherein the latex starting material latex dispersion has a particle size of about 500–1500 Å.

16. The method of claim 8, wherein the latex starting material latex has a polymer solids content of about 1–50 percent.

17. The method of claim 1, wherein the aqueous phase comprises 1–20 percent by weight of a surfactant.

18. The method of claim 17, wherein the surfactant comprises a non-ionic surfactant.

19. The method of claim 1, wherein the temperature of step (c) is about ambient temperature.

20. The method of claim 7, comprising:
(a) dissolving an amount of tridiphane equal to about 75–95 percent by weight of the content of polymer solids in the latex in about 0.7–1 ml/g of hexane;
(b) introducing the resultant solution to an aqueous polystyrene latex having a polymer solids content of about 1–50 percent, a polymer particle size of 500–1500 Å, an aqueous phase containing 2–15 percent by weight, relative to polymer solids content, of a surfactant and wherein said dispersion is stabilized with itaconic acid;
(c) agitating the resultant mixture until substantially all of the tridiphane is absorbed into the polymer solids; and
(d) subjecting the resultant mixture to reduce pressure until the hexane is removed therefrom.

* * * * *